US011298385B2

(12) United States Patent
Chung

(10) Patent No.: US 11,298,385 B2
(45) Date of Patent: *Apr. 12, 2022

(54) MICROORGANISM FOR DELIVERING DRUG FOR TREATMENT OF GASTROINTESTINAL DISEASE, WHICH EXPRESSES AND SECRETES P8 PROTEIN, AND PHARMACEUTICAL COMPOSITION FOR PREVENTING OR TREATING GASTROINTESTINAL DISEASE, WHICH INCLUDES THE SAME

(71) Applicant: CELL BIOTECH CO., LTD., Gimpo-si (KR)

(72) Inventor: Myung Jun Chung, Seoul (KR)

(73) Assignee: Cell Biotech Co., Ltd., Gimpo-si (KR)

( * ) Notice: Subject to any disclaimer, the term of this patent is extended or adjusted under 35 U.S.C. 154(b) by 132 days.

This patent is subject to a terminal disclaimer.

(21) Appl. No.: 16/471,940

(22) PCT Filed: Oct. 16, 2018

(86) PCT No.: PCT/KR2018/012164
§ 371 (c)(1),
(2) Date: Jun. 20, 2019

(87) PCT Pub. No.: WO2019/139229
PCT Pub. Date: Jul. 18, 2019

(65) Prior Publication Data
US 2019/0328801 A1 Oct. 31, 2019

(30) Foreign Application Priority Data
Jan. 9, 2018 (KR) .......................... 10-2018-0003008

(51) Int. Cl.
| | |
|---|---|
| *A01N 63/00* | (2020.01) |
| *A61K 39/00* | (2006.01) |
| *A61K 39/02* | (2006.01) |
| *C07H 21/02* | (2006.01) |
| *A61K 35/747* | (2015.01) |
| *C07K 14/47* | (2006.01) |
| *C12N 1/20* | (2006.01) |
| *C12N 15/74* | (2006.01) |
| *C12N 15/62* | (2006.01) |
| *A61K 38/16* | (2006.01) |
| *A61K 35/745* | (2015.01) |
| *A61K 35/744* | (2015.01) |
| *C12R 1/23* | (2006.01) |
| *C12R 1/24* | (2006.01) |
| *C12R 1/245* | (2006.01) |
| *A61K 38/00* | (2006.01) |
| *A61K 35/74* | (2015.01) |

(52) U.S. Cl.
CPC .......... *A61K 35/747* (2013.01); *A61K 35/744* (2013.01); *A61K 35/745* (2013.01); *A61K 38/164* (2013.01); *C07K 14/47* (2013.01); *C12N 1/20* (2013.01); *C12N 1/205* (2021.05); *C12N 15/625* (2013.01); *C12N 15/74* (2013.01); *C12N 15/746* (2013.01); *A61K 35/74* (2013.01); *A61K 38/00* (2013.01); *A61K 2039/522* (2013.01); *C12R 2001/23* (2021.05); *C12R 2001/24* (2021.05); *C12R 2001/245* (2021.05)

(58) Field of Classification Search
CPC .................................................... A61K 35/747
See application file for complete search history.

(56) References Cited

U.S. PATENT DOCUMENTS

| | | | |
|---|---|---|---|
| 2002/0137140 A1 | 9/2002 | Vrang et al. | |
| 2012/0315249 A1 | 12/2012 | Olmstead | |
| 2016/0281053 A1* | 9/2016 | Sorek | C07K 14/245 |
| 2019/0328800 A1* | 10/2019 | Chung | C12N 15/746 |

FOREIGN PATENT DOCUMENTS

| | | |
|---|---|---|
| JP | 2004-511248 A | 4/2004 |
| KR | 2009-0114279 | 11/2009 |
| KR | 2011-0073897 | 6/2011 |
| KR | 2014-0053950 A | 5/2014 |
| KR | 10-1656208 B1 | 9/2016 |
| WO | 2014/037505 A1 | 3/2014 |

OTHER PUBLICATIONS

Sanger et al. (Therap Adv Gastroenterol. Sep. 2010; 3(5):291-305) (Year: 2010).*
Clevelandclinic.org, https://my.clevelandclinic.org/health/articles/7040-gastrointestinal-disorders, 16 pages, accessed Mar. 27, 2020 (Year: 2020).*
NCBI Reference Sequence: WP_005686763.1, May 8, 2013, 2 pages.
Sadeghi-Aliabadi, H. et al., "Effects of Lactobacillus plantarum A7 with probiotic potential on colon cancer and normal cells proliferation in comparison with a commercial strain", Iranian Journal of Basic Medical Sciences, Oct. 2014, vol. 17, No. 10, pp. 815-819.
International Search Report and Written Opinion issued for International Application No. PCT/KR2018/012164, dated Feb. 1, 2019, 9 pages.

* cited by examiner

*Primary Examiner* — Gary B Nickol
*Assistant Examiner* — Lakia J Jackson-Tongue
(74) *Attorney, Agent, or Firm* — Hamre, Schumann, Mueller & Larson, P.C.

(57) ABSTRACT

The present invention relates to a microorganism for drug delivery, which has been transformed with a gene construct comprising a therapeutically active peptide, which can be delivered safely into the intestines through oral administration, and which can express and secrete the therapeutic peptide in the gastrointestinal tract, and also relates to a pharmaceutical composition for prevention or treatment of gastrointestinal disease, which includes the same. The present invention is directed to a lactic acid bacteria drug delivery system capable of overexpressing and secreting a lactic acid bacteria-derived anticancer protein, which is developed by introducing the anticancer protein into a lactic acid bacteria expression and secretion system. It is expected that the lactic acid bacteria drug delivery system will be widely used as a natural protein therapeutic agent against gastrointestinal disease in the medical field.

9 Claims, 7 Drawing Sheets

Specification includes a Sequence Listing.

| P8 protein secretion | |
|---|---|
| Promoter | ug/L |
| ChoS | 66.3±1.3 |
| G6PI | 121.4±5.9 |
| GK | 139.0±11.2 |
| L-ldh | 138.6±24.0 |
| PK | 137.3±9.7 |
| ErmE | 75.1±11.8 |
| 6PFK | 72.8±30.5 |

Promoter name

ChoS: choline ABC transporter permease promoter
G6PI: glucose-6-phosphate isomerase promoter
GK: glucokinase promoter
L-ldh: L-lactate dehydrogenase promoter
PK: pyruvate kinase promoter
ErmE: erythromycin E
6PFK: 6-phosphofructokinase promoter

US 11,298,385 B2

MICROORGANISM FOR DELIVERING DRUG FOR TREATMENT OF GASTROINTESTINAL DISEASE, WHICH EXPRESSES AND SECRETES P8 PROTEIN, AND PHARMACEUTICAL COMPOSITION FOR PREVENTING OR TREATING GASTROINTESTINAL DISEASE, WHICH INCLUDES THE SAME

TECHNICAL FIELD

The present invention relates to a microorganism for delivering a drug for treating gastrointestinal disease, which expresses and secretes P8 protein, and a composition for preventing or treating gastrointestinal disease, which includes the same, and more specifically to a microorganism for locally delivering a polypeptide for treatment of gastrointestinal disease, such as an anticancer active protein, into the gastrointestinal tract via an oral route, and a composition for preventing or treating gastrointestinal disease, including the same.

STATEMENT AS TO GOVERNMENT-FUNDED RESEARCH

This invention was made with Korean Government support under a grant No. 52367890 funded by the Ministry of Trade, Industry and Energy, under the supervision of the Republic of Korea Small and Medium Business Administration, from the WC300 project for developing drug-delivery probiotics for treatment of inveterate intestinal disease, study period was 2016 Feb. 1-2020 Dec. 31.

BACKGROUND ART

Lactic acid bacteria are microorganisms widely distributed in nature, and produce lactic acid by anaerobic fermentation of carbohydrates. Due to their advantage of being non-pathogenic bacteria, lactic acid bacteria have recently been widely used in industrial fields as well as in medical fields.

Currently, the number of patients with gastrointestinal disease is increasing drastically due to the effects of frequent stress, westernized eating habits, drinking, and the like. For treatment of colorectal cancer, synthetic compounds have been developed and used, including flouropyrimidine-based drugs, such as 5-fluorouracil (5-FU), UFT (tegafur-uracil) and capecitabine, as well as irinotecan, oxaliplatin, and the like. In addition, targeted therapeutic agents have been used, including bevacizumab (trade name: Avastin), cetuximab (trade name: Erbitux) and the like. However, they have a high risk of adverse effects associated with high-dose administration and long-term use, and, for this reason, the development of natural therapeutic agents is urgently required.

It is known that administration of lactic acid bacteria to patients with colorectal diseases including colorectal cancer and colitis can exhibit therapeutic effects. Thus, technologies have been developed to use lactic acid bacteria as agents for treating colorectal diseases. For example, Korean Patent Application Publication No. 2011-0073897 discloses an anticancer composition including *Lactobacillus plantarum* PMO 08 (KFCC-11028) as an active ingredient, and Korean Patent Application Publication No. 2009-0114279 discloses an anticancer pharmaceutical composition including, as an active ingredient, a butanol extract of a *Bifidobacterium adolescentis* SPM0212 strain having cancer cell growth inhibitory activity, deposited under accession number KCTC 18120P. However, conventional technologies to use lactic acid bacteria against gastrointestinal diseases use lactic acid bacteria themselves, and there has been little attempt to transform lactic acid bacteria with a gene encoding an anticancer active protein in order to use the lactic acid bacteria strain itself as a drug delivery system.

DISCLOSURE

Technical Problem

The present invention has been conceived to overcome the above-described conventional drawbacks, and an object of the present invention is to provide a microorganism for delivering a therapeutic peptide effective against gastrointestinal disease to a specific site in the gastrointestinal tract, wherein the microorganism has been transformed with a gene encoding the therapeutic peptide and is capable of acting as a drug delivery system.

Another object of the present invention is to provide a pharmaceutical composition for preventing or treating gastrointestinal disease, which includes a microorganism as a drug delivery system which is used to deliver a substance beneficial for treatment of gastrointestinal disease to a specific site in the gastrointestinal tract and which is capable of expressing and secreting a therapeutically effective high level of biologically active polypeptide at a predetermined location in the gastrointestinal tract.

Technical Solution

One aspect of the present invention to achieve the above-described objects is directed to a microorganism for delivering a drug for treatment of gastrointestinal disease, wherein the microorganism has been transformed with a gene construct, including a P8 protein-encoding polynucleotide operably linked to an exogenous promoter and having a nucleotide sequence represented by SEQ ID NO: 1 and a gene encoding a secretion signal peptide, and expresses and secretes the P8 protein in the gastrointestinal tract.

The exogenous promoter is at least one promoter selected from the group consisting of SEQ ID NO: 3 (ermE promoter), SEQ ID NO: 4 (PK promoter), SEQ ID NO: 5 (GK promoter), SEQ ID NO: 6 (GPFK promoter), SEQ ID NO: 7 (G6Pi promoter), SEQ ID NO: 8 (L-LDH promoter), and combinations thereof, derived from *Pediococcus pentosaceus*.

The strain may belong to the genus *Lactobacillus, Latococcus, Leuconostoc, Pediococcus*, or *Bifidobacterium*.

Specific examples of the strain include *Lactobacillus rhamnosus, Lactobacillus acidophilus, Lactobacillus paracasei, Lactobacillus plantarum, Pediococcus pentosaceus*, or *Lactobacillus brevis* strains. Preferably, the strain may be a *Pediococcus pentosaceus* strain.

The secretion signal peptide is a USP45 secretion signal peptide, Usp45 N4 or a *Lactobacillus brevis* S-layer protein signal peptide.

The gene construct transformed into the microbial strain as a drug delivery system may further include, downstream of the promoter, a second promoter, a second secretion signal peptide, and a heterologous nucleic acid sequence encoding a second therapeutic peptide. The second promoter may be the same as or different from the first promoter.

The strain of the present invention may be used for prevention or treatment of gastrointestinal diseases, such as colorectal cancer, colon polyps, colitis, ischemic gastrointestinal diseases, dysentery, intestinal vascular dysplasia, diverticulosis, irritable bowel syndrome, and Crohn's disease.

Another aspect of the present invention to achieve the above-described objects is directed to a pharmaceutical composition for prevention or treatment of gastrointestinal disease, including a strain that produces a P8 protein having an amino acid sequence represented by SEQ ID NO: 2.

Still another aspect of the present invention to achieve the above-described objects is directed to a pharmaceutical composition for prevention or treatment of gastrointestinal disease, including a *Pediococcus pentosaceus* strain, wherein the *Pediococcus pentosaceus* strain includes a heterologous nucleic acid encoding a therapeutic peptide having a therapeutic effect against at least one gastrointestinal disease, wherein the heterologous nucleic acid includes: at least one promoter operably linked to the heterologous nucleic acid and selected from the group consisting of SEQ ID NOs: 3 to 8 and combinations thereof, derived from *Pediococcus pentosaceus*; and a gene encoding a secretion signal peptide.

Advantageous Effects

A microbial strain for drug delivery, which includes a promoter isolated from the glycolysis pathway of lactic acid bacteria according to the present invention, is capable of effectively functioning as a drug delivery system by continuously expressing and secreting a high level of therapeutically active peptide while residing in the intestines.

Furthermore, the microorganism of the present invention is obtained by transforming lactic acid bacteria with a gene construct encoding a human natural protein confirmed to inhibit the growth and metastasis of cancer cells, and thus can maximize therapeutic effects without side effects.

The pharmaceutical composition of the present invention is a safe substance which not only exhibits an excellent inhibitory effect against the growth of colorectal cancer cells, but is also not toxic to normal cells, indicating that it may advantageously be used for the prevention and treatment of colorectal cancer.

According to the present invention, a therapeutic peptide synthesized in situ by the recombinant microorganism can be delivered locally via an oral route, and thus the dose and treatment timing necessary for treatment can be precisely controlled, thereby eliminating the need for systemic administration.

The present invention may advantageously be used for local delivery of a substance which is unstable or difficult to produce in large amounts. According to the present invention, it is possible to continuously and locally deliver a therapeutic peptide at higher concentrations than those obtained by systemic, delivery without side-effect problems.

MODE FOR INVENTION

Figure 1:
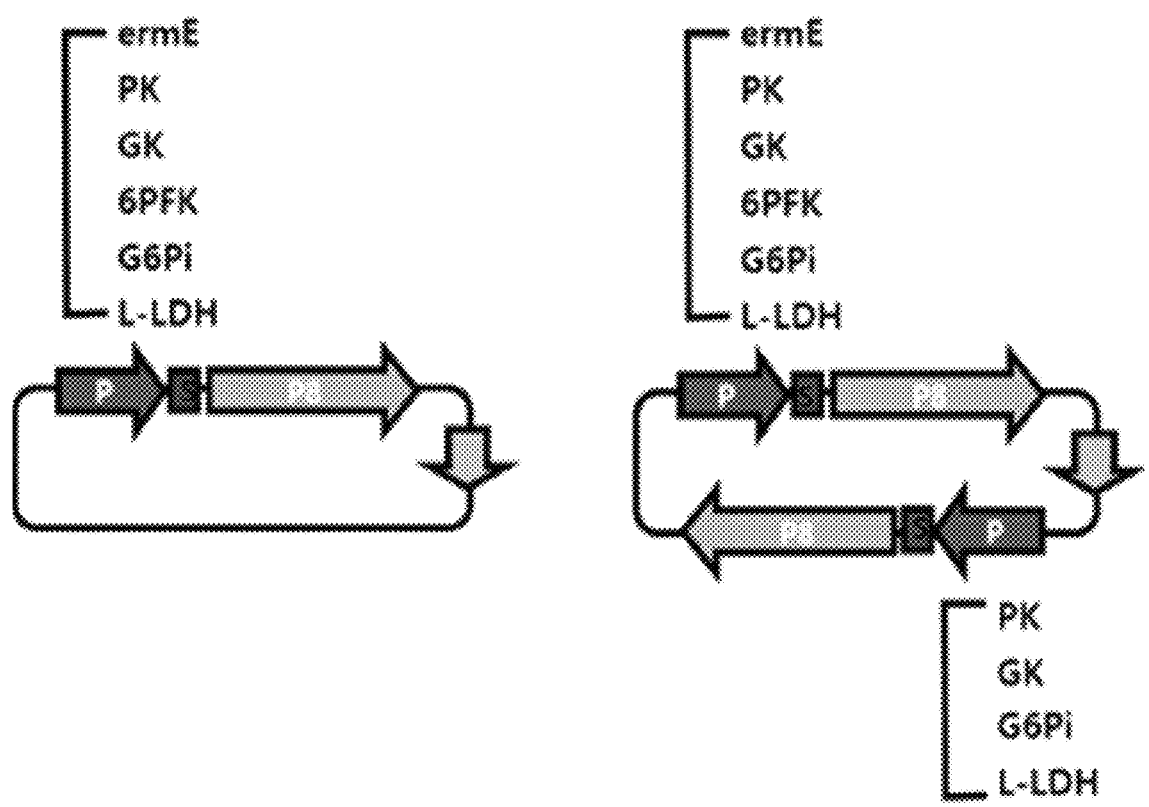
FIG. 1 is a view showing the configurations of expression vectors, including a single promoter and two promoters, respectively, used to transform a *Pediococcus pentosaceus* strain in an example of the present invention.
Figure 2:
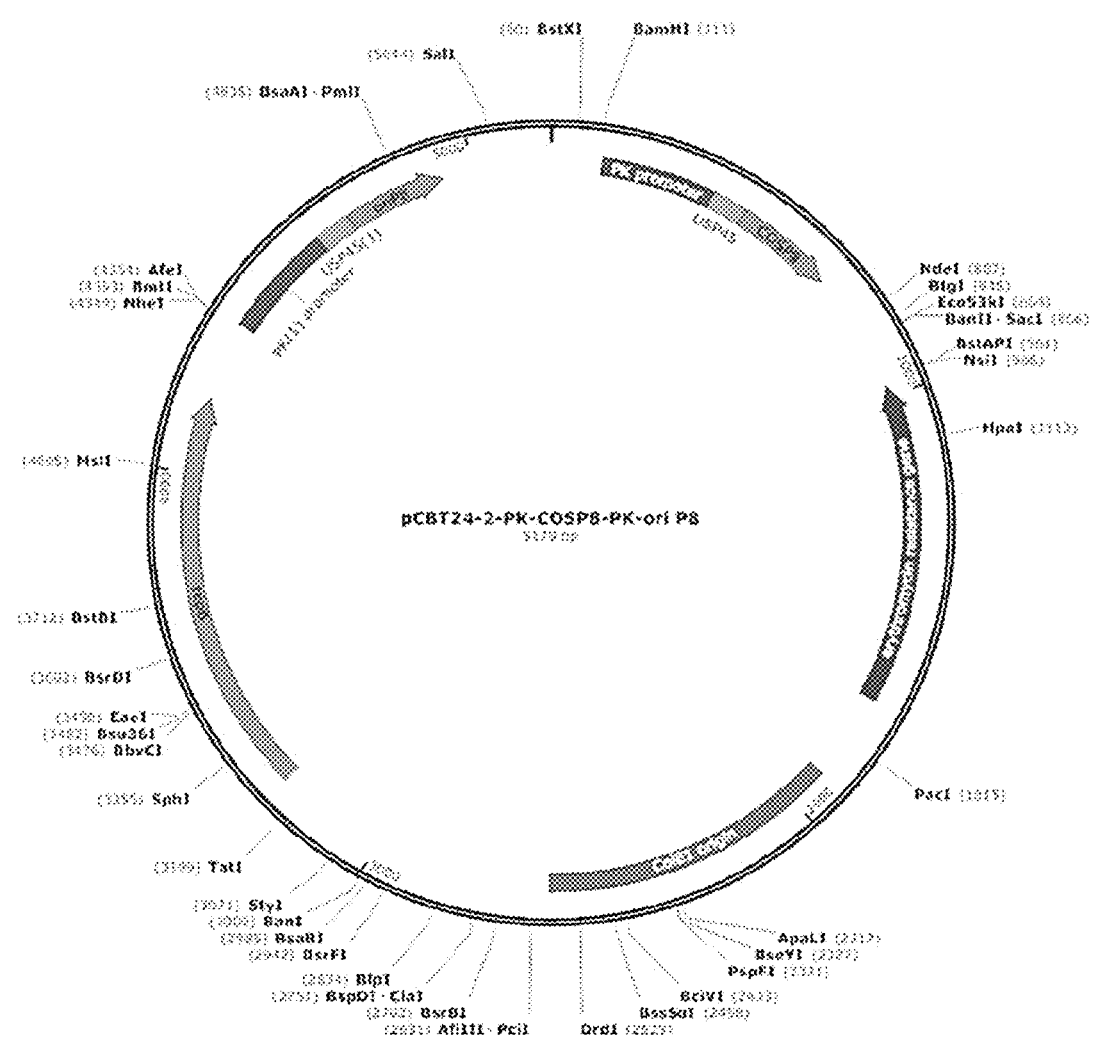
FIG. 2 is a cleavage map of an expression vector used to transform a *Pediococcus pentosaceus* strain in an example of the present invention.
Figure 3:
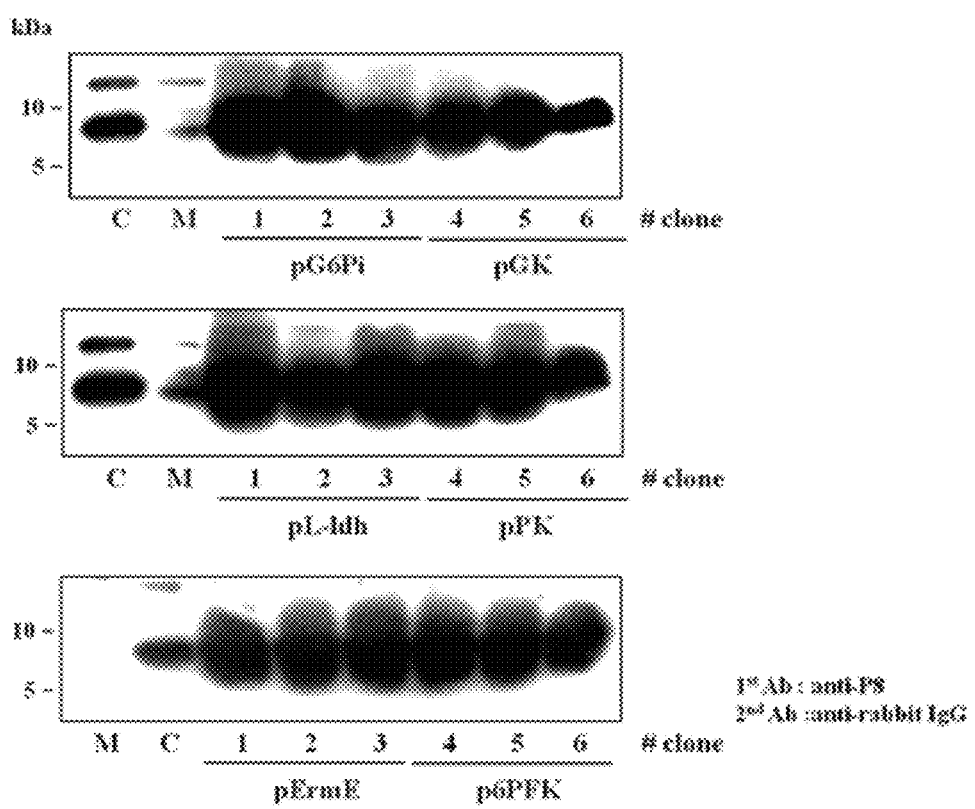
FIG. 3 is a photograph showing the results of Western blotting analysis performed to qualitatively analyze the expression level of P8 protein by a recombinant strain cloned with a P8 protein-encoding gene according to the present invention.
Figure 4:
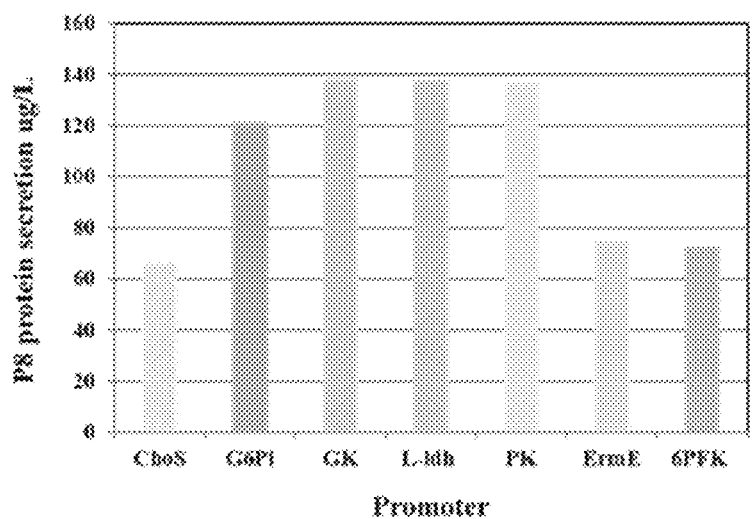
FIG. 4 is a photograph showing the results of ELISA performed to quantitatively analyze the changes in expression/secretion levels of P8 protein by a recombinant strain cloned with a P8 protein-encoding gene according to the present invention.
Figure 5:
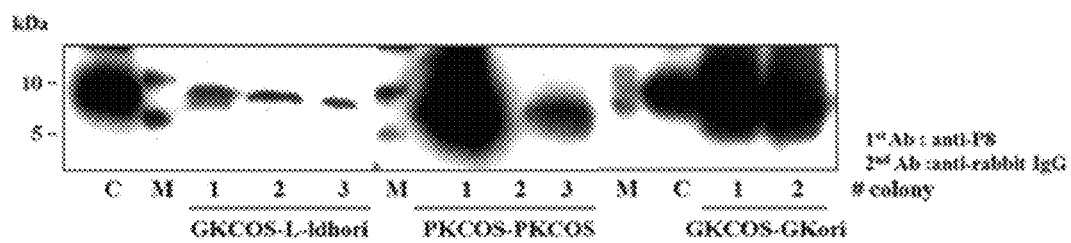
FIG. 5 is a view showing the results of Western blotting performed to qualitatively analyze the changes in expression/secretion levels of P8 protein by a combination of two promoters (PK-PK)
Figure 6:
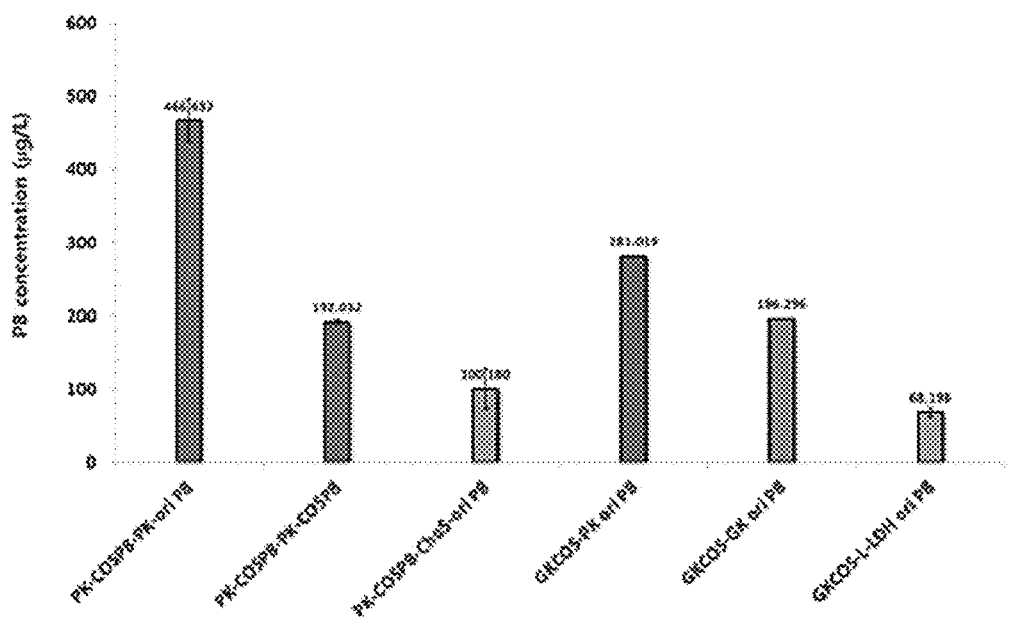
FIG. 6 is a graph showing the results of ELISA performed to quantitatively analyze the changes in expression/secretion levels of P8 protein by a combination of two promoters (PK-PK)

The present invention will be described in more detail below with reference to the accompanying drawings.

Unless otherwise defined, all the scientific and technical terms used in the specification have the same meanings as commonly understood by those skilled in the technical field to which the present invention.

The term "nucleic acid" refers to a deoxyribonucleotide or ribonucleotide polymer in either single- or double-stranded form, and unless otherwise limited, encompasses known analogs of natural nucleotides that that hybridize to nucleic acids in a manner similar to naturally occurring nucleotides. Unless, otherwise indicated, a particular nucleic acid sequence includes its complementary sequence.

As used herein, the term "promoter" refers to a DNA sequence capable of controlling the expression of a coding sequence or functional RNA. Any person skilled in the art will easily recognize a promoter region. The promoter consists of proximal and distal upstream elements. Proximal elements include a TATA box capable of directing RNA polymerase II to initiate RNA synthesis at an appropriate transcription initiation site.

The term "biologically active molecule" refers to substances which are involved in gene therapy or capable of regulating immune responses, and include substances capable of regulating intracellular signal transduction mechanisms or the expression of other particular genes. These substances may include growth factors, substances for cancer treatment, tumor suppressors, cytokines, interferons, and the like.

As used herein, a "heterologous sequence" or a heterologous nucleic acid" means one that originates from a foreign source (or species) or, if originates from the same source, is modified from its original form. Thus, a heterologous nucleic acid operably linked to a promoter is derived from a source different from that from which the promoter was derived, or, if derived from the same source, is modified from its original form.

The term "operably linked" refers to functional linkage between a nucleic acid expression control sequence (such as a promoter, signal sequence, or array of transcription factor binding sites) and a heterologous nucleic acid sequence, wherein the expression control sequence affects transcription and/or translation of the nucleic acid corresponding to the heterologous nucleic acid sequence.

As used herein, the terms "protein" and "polypeptide" are used interchangeably. A "polypeptide" refers to a polymer of amino acids, and does not refer to a specific length of the molecule. This term also includes post-translational modifications of the polypeptide, such as glycosylation, phosphorylation and acetylation.

As used herein, the term "prevention" means a medical or public health procedure whose purpose is to prevent disease rather than to treat or cure disease.

As used herein, the term "treatment" means a medical or public health procedure whose purpose is to treat or cure disease.

As used herein, the term "therapeutically effective amount" refers to the amount of therapeutic substance or composition effective to treat a disease or disorder in a subject, e.g., human or animal, i.e., to obtain a desired local or systemic effect and performance.

As used herein, the term "pharmaceutically acceptable" means compatible with the other ingredients of a pharmaceutical composition and not deleterious to the recipient thereof.

One aspect of the present invention is directed to a microorganism for delivering a drug for treatment of gastrointestinal disease, wherein the microorganism has been transformed with a gene construct, including a P8 protein-encoding polynucleotide operably linked to an exogenous promoter and having a nucleotide sequence represented by SEQ ID NO: 1 and a gene encoding a secretion signal peptide, and expresses and secretes the P8 protein in the gastrointestinal tract.

In one embodiment of the present invention, the "P8 protein" is an 8-kDa protein fragment extracted from the lactic acid bacterium *Lactobacillus rhamnosus*, which is an anticancer protein derived from a *Lactobacillus rhamnosus* cell lysate.

The microorganism for delivering a drug for treatment of gastrointestinal disease according to the present invention, which expresses and secretes the P8 protein in the gastrointestinal tract, may exhibit synergistic effects by the anticancer effect of the lactic acid bacteria themselves in addition to the anticancer effect of the P8 protein. Lactic acid bacteria strains may exhibit the effect of inhibiting the production of carcinogenic substances by improvement of intestinal microbiota and the effect of inhibiting cancer cell proliferation by the activation of intestinal immune functions.

TABLE 1

| SEQ ID NO | Definition | Sequence |
| --- | --- | --- |
| SEQ ID NO: 1 | Nucleotide sequence of P8 protein | gcaacagtagatcctgaaaagacattgtttctcgatgaaccaatga acaaggtatttgactggagcaacagcgaagcacctgtacgtgatgc gctgtgggattattacatggaaaagaacagccgtgataccatcaag actgaagaagaaatgaaaccagtcctagacatgtccgacgatgagg tcaaagccctagcagaaaaggttctcaagaagtaa |
| SEQ ID NO: 2 | Amino acid sequence of P8 protein | ATVDPEKTLFLDEPMNKVFDWSNSEAPVRDALWDYYMEKNSRDTIK TEEEMKPVLDMSDDEVKALAEKVLKK |

In the present invention, five strong promoters for expression of a target protein in lactic acid bacteria were selected. The exogenous promoter may be selected from SEQ ID NO: 3 (ermE, erythromycin resistance gene), SEQ ID NO: 4 (PK promoter, pyruvate kinase), SEQ ID NO: 5 (GK promoter, glucokinase), SEQ ID NO: 6 (GPFK promoter, 6-phosphofructokinase), SEQ ID NO: 7 (G6Pi promoter, glucose 6-phosphate isomerase), SEQ ID NO: 8 (L-LDH promoter, L-lactate dehydrogenase), and combinations thereof, derived from *Pediococcus pentosaceus*.

TABLE 2

| Primer | Sequence (5' → 3') |
| --- | --- |
| ermE | GGATCCTTTTTAGTATTTTTAATTAATTGTAATCAGCACAGTTCATTATCAACCAAACAAAA AATAAGTGGTTATAATGAATCGTTAATAAGCAAAATTCATATAACCAAATTAAAGAGGGTTA TAATGAAAAAAAAGATTATCTCAGCTATTTTAATGTCTACAGTGATACTTTCTGCTGCAG |
| PK | GGATCCCTAAAGATCGCGTTTTAGCAAGTAAGATGGGTGCTTACGCTGTTGAGCTACTCCTT GAAGGTAAGGGTGGTTTAGCAGTTGGAATCTTAGAAAATAAGGTTCAAGCTCATAACATGCT TGACTTGTTTGATGCAAAACATCAAGCAGATGATTCACTTTACCAATTAAGTGAAGATTTAT CATTCTAGAGTTCTATTAATATTTGGATAAAATGACTTAAGAAGTCTTTTATAATTTAAAAT CAAGGGAGAGATTCTGTAATGAAAAAAAAGATTATCTCAGCTATTTTAATGTCTACAGTGAT ACTTTCTGCTGCAG |

TABLE 2-continued

| Primer | Sequence (5' → 3') |
|---|---|
| GK | GGATCCATAATCTGGTAAATTAGTTGAGATGGTATTATGAAAACACTTTATGATGTGCAACA<br>ACTTTTAAAGCAATTCGGAATATTTGTTTACGTTGGAAAACGTAAATGGGATATTGAATTGA<br>TGAGTATTGAATTGAAAAATTTGTACAAAGCAGGAGTCGTCGATAAACCGACTTATGTTAAA<br>GCTCAGTTGGTTTTACGACATGAGCATCATATTGAAGAGGTTAGAGATAACCAACAAAAATA<br>ATGGAGGGTTTCGAAGTAATGAAAAAAAAGATTATCTCAGCTATTTTAATGTCTACAGTGAT<br>ACTTTCTGCTGCAG |
| GPFK | GGATCCCCAGTTATTTTAGTTTATGAGGATACTAATGAACATAATGAGTTGTCTGAAAAATT<br>TTATTTAAATGACAGTTCTGAAGTAAAAGAACAATTAGCAGAATTGCTAGGAAGTCAACATA<br>TTTCGTTAATTAAAAAATAAATTTTGAATAAAGCACTTACATTCGATTAATTAAGAAAATGG<br>TACAGACAACTGTTTTCAAAAGTGATAAAATCAACAATGAAGTTTTGAAAAAACTCAATATT<br>TCTGTTTGAGGTGAAAAGATGAAAAAAAAGATTATCTCAGCTATTTTAATGTCTACAGTGAT<br>ACTTTCTGCTGCAG |
| G6Pi | GGATCCATGCCGGCTAAAGTGGTGGATAAATTGAATCATCCCCAAGAACTGGAATAAGATAA<br>AATTGTAGTGCTTTCAGGCTTTACCAGCCATCTTTTGAAAAAATTAATTTCTTTCAAAAGTG<br>CGTGTGACAGGTGATCAACTAGATTAAATGGGGAGGGTATCCCAGTAAATATTAGGTTAAAT<br>CGGATAGGCTTAACCAAATTAAGTAATTTTATTGTATAATGGTACAGATAAAGAATTTTAAA<br>CAAAAGGGGTAGTTATTAATGAAAAAAAAGATTATCTCAGCTATTTTAATGTCTACAGTGAT<br>ACTTTCTGCTGCAG |
| L-LDH | GGATCCTCATTTTCATGTTATTTTTCCACCCTCAACACGCAAAAACGGCTGAAAGAGCAAAA<br>ACCCCTCAGCTGTCCACGTTTATTTTCATGTAATATTACCATATTATTGACCCCAAGCGGGT<br>CTTTTAACCTCTAACTTATCAATCACTTTACTAACTATACCCGAACTTCATAAAATTTTTAC<br>TCAACTTTCTTTTATGAAAATGCTATACTTAGTATTGTTTGATAAATTCAAATATTATATGA<br>AAAAAGGGGATTGATCTTATGAAAAAAAAGATTATCTCAGCTATTTTAATGTCTACAGTGAT<br>ACTTTCTGCTGCAG |

The promoters, when introduced into microbial cells, promote the expression of a heterologous nucleic acid encoding a biologically active foreign protein. Of the promoters of SEQ ID NO: 3 to SEQ ID NOs: 8, five (ermE promoter, PK promoter, GK promoter, GPFK promoter, and G6Pi promoter) were selected from the glycolysis metabolic pathway of *Pediococcus pentosaceus*, and one (L-LDH promoter) was selected from the secondary metabolite lactate production pathway. These promoters are strong promoters that induce high-level expression of a heterologous nucleic acid in lactic acid bacteria (e.g., *Pediococcus pentosaceus*). These promoters enable the microorganism of the present invention to function as a drug delivery system and to produce and secrete a sufficient amount of the P8 protein at a specific site in the gastrointestinal tract.

The gene construct may increase not only the expression level of a heterologous nucleic acid but also secretion of the heterologous nucleic acid. As used herein, the expression "protein is secreted" means that the protein is transported extracellularly from microbial cells, and this expression includes the case in which the entire protein molecule is substantially present in medium in a completely released form, and also includes the case in which the entire protein molecule is present in the cell surface layer, and the case in which a portion of the protein molecule is present in medium while the remaining portion of the molecule is present in the cell surface layer.

The gene construct may also include a replication origin replicable in microbial cells. The reason for this is that manipulation of the vector is more efficient in lactic acid bacteria strain, and preferred examples of the replication origin include ColE1, Ori, oriT, and the like.

The gene construct may include a secretion signal peptide sequence suitable for allowing the therapeutic peptide to be secreted or released from a microbial drug delivery system (e.g., a *Pediococcus pentosaceus* system). To allow secretion of the therapeutic peptide, a fragment encoding a secretion signal peptide suitable for use in *Pediococcus pentosaceus* may be added to the 5' end or 3' end of the heterologous nucleic acid sequence.

The secretion signal peptide may include a secretion signal peptide that directs strong protein secretion, such as a USP45 secretion signal, Usp45 N4 in which lysine at position 4 of a wild-type Usp45 secretion signal is substituted with asparagine, or a *Lactobacillus brevis* S-layer protein signal peptide. This secretion signal peptide is capable of providing the secretion of the exogenous protein of interest. In addition, this secretion signal peptide sequence can additionally control the production and secretion of the therapeutic polypeptide of interest.

In another embodiment of the present invention, the gene construct may further include, downstream of the promoter, a second promoter other than the above-described promoter of any one of SEQ ID NOs: 3 to 8, a second secretion signal peptide, and a second nucleic acid sequence encoding a therapeutic polypeptide.

In another embodiment of the present invention, the gene construct may necessarily have a first promoter upstream of the heterologous nucleic acid to be expressed, and may also include a second promoter downstream of the heterologous nucleic acid to be expressed. The first promoter and the second promoter may be the same as or different from each other. It is possible to use not only a non-specific promoter capable of promoting the expression of a foreign gene in most cells or tissues, but also a specific or selective promoter, such as a tissue- or organ-specific promoter, a tumor-specific promoter, a development- or differentiation-specific promoter or the like. For example, a specific promoter may be used as the first promoter, and a non-specific promoter may be used as the second promoter. A microorganism transformed with a gene construct including these two promoters is capable of expressing a desired heterologous polypeptide or protein in a very high yield.

The microbial strain may be a strain belonging to the genus *Lactobacillus, Latococcus, Leuconostoc, Pediococcus*, or *Bifidobacterium*. Specific examples of the strain include, but are not necessarily limited to, *Lactobacillus*

*rhamnosus, Lactobacillus acidophilus, Lactobacillus paracasei, Lactobacillus plantarum, Pediococcus pentosaceus,* or *Lactobacillus brevis* strains.

Preferably, the strain may be a *Pediococcus pentosaceus* strain (e.g., KCCM12181P). *Pediococcus pentosaceus* can survive during passage through the gastrointestinal tract due to its excellent acid resistance and bile juice resistance, and reach and adhere well to the intestinal mucosal layer in a living form, indicating that it can continuously function as a drug delivery system.

The strain that is used as a drug delivery system preferably *Pediococcus* PP P8 deposited under accession number KCCM12181P, but any strains for delivering a drug for treatment of gastrointestinal disease, which expresses and secretes the P8 protein of the present invention, are all included in the scope of the present invention.

The microorganism of the present invention is obtained by transfecting a microbial strain with an expression vector including the gene construct, and thus a heterologous nucleic acid encoding a desired therapeutic peptide can be expressed by the microbial strain at a predetermined location in the gastrointestinal tract, thereby producing the therapeutic peptide.

Another aspect of the present invention is directed to a pharmaceutical composition for prevention or treatment of gastrointestinal disease, which includes the above-described microbial strain that produces and secretes the P8 protein having the amino acid sequence represented by SEQ ID NO: 2.

Still another aspect of the present invention is directed to a pharmaceutical composition for prevention or treatment of gastrointestinal disease, including a *Pediococcus pentosaceus* strain, wherein the *Pediococcus pentosaceus* strain includes a heterologous nucleic acid encoding a therapeutic peptide having a therapeutic effect against at least one gastrointestinal disease, wherein the heterologous nucleic acid includes: at least one promoter operably linked to the heterologous nucleic acid and selected from SEQ ID NOs: 3 to 8 and combinations thereof, derived from *Pediococcus pentosaceus*; and a gene encoding a secretion signal peptide.

The heterologous nucleic acid may preferably encode a therapeutic peptide or a disease-related polypeptide. In addition, the heterologous nucleic acid may encode an antigenic polypeptide for use as a vaccine. In the present invention, the heterologous nucleic acid may be a gene encoding a hormone, a cytokine, an enzyme, a coagulation factor, a transporter protein, a receptor, a regulatory protein, a structural protein, a transcription factor, an antigen, an antibody or the like. Specific examples thereof include, but are not limited to, genes encoding thrombopoietin, growth hormones, growth hormone-releasing hormones, growth hormone-releasing peptides, interferons, interferon receptors, colony-stimulating factors, glucagon-like peptides, G-protein coupled receptors, interleukins, interleukin receptors, enzymes, interleukin binding proteins, cytokine binding proteins, macrophage activators, macrophage peptides, B-cell factors, T-cell factors, protein A, allergy inhibitors, necrosis glycoproteins, immunotoxins, lymphotoxins, tumor necrosis factors, tumor suppressors, transforming growth factors, α-1 anti-trypsin, albumin, α-lactalbumin, apolipoprotein-E, erythropoietin, highly glycosylated erythropoietin, angiopoietin, hemoglobin, thrombin, thrombin receptor activating peptides, thrombomodulin, blood factors VII, VIIa, VIII, IX and XIII, plasminogen activators, fibrin-binding peptides, urokinases, streptokinases, hirudin, protein C, C-reactive proteins, superoxide dismutase, leptin, platelet-derived growth factors, epithelial growth factors, epidermal growth factors, angiostatin, angiotensin, bone growth factors, bone stimulating proteins, calcitonin, insulin, atriopeptin, cartilage inducing factors, elcatonin, connective tissue activating factors, follicle stimulating hormones, luteinizing hormones, luteinizing hormone releasing hormones, nerve growth factors, parathyroid hormones, relaxin, secretin, somatomedin, insulin-like growth factors, adrenocortical hormones, glucagon, cholecystokinin, pancreatic polypeptides, gastrin releasing peptides, corticotropin releasing factors, thyroid stimulating hormones, autotaxin, lactoferrin, myostatin, receptors, receptor antagonists, cell surface antigens, virus derived vaccine antigens, monoclonal antibodies, polyclonal antibodies, antibody fragments, and the like.

Gastrointestinal diseases suitable for treatment with the pharmaceutical composition of the present invention includes diseases and disorders that affect organs, such as the mouth, esophagus, stomach, small intestine, large intestine, rectum, pancreas, liver and gallbladder. For examples, the diseases include dry mouth, oral ulcer, gingival diseases, gastroesophageal reflux diseases, gastric ulcer, inflammatory bowel diseases, inflammatory colitis, Crohn's disease, mycositis, gastric cancer, and colorectal cancer. In particular, the pharmaceutical composition may advantageously be used for treatment of colorectal cancer, colitis, irritable bowel syndrome, and Crohn's disease.

The *Pediococcus pentosaceus* strain can survive during passage through the gastrointestinal tract due to its excellent acid resistance and bile juice resistance, and reach and adhere well to the intestinal mucosal layer in a living form, indicating that it can continuously function as a drug delivery system.

Still another aspect of the present invention is directed to a pharmaceutical composition for prevention or treatment of gastrointestinal disease, which includes the strain of the present invention, that is, a microorganism which has been transformed with a gene construct, including a P8 protein-encoding polynucleotide operably linked to an exogenous promoter and a gene encoding a secretion signal peptide, and which expresses and secretes the P8 protein in the gastrointestinal tract.

The secretion signal peptide may be a secretion signal peptide, such as a USP45 secretion signal peptide, Usp45 N4 or a *Lactobacillus brevis* S-layer protein signal peptide.

The strain may further include, downstream of the promoter, a second promoter, a second signal peptide, and a heterologous nucleic acid sequence encoding a second therapeutic peptide, and the second promoter may be the same as or different from the first promoter. The heterologous nucleic acid sequence encoding the first therapeutic peptide and the heterologous nucleic acid sequence encoding the second therapeutic peptide may be the same as or different from each other. In another example, the nucleotide sequence of the heterologous nucleic acid sequence encoding the first therapeutic peptide and the nucleotide sequence of heterologous nucleic acid sequence encoding the second therapeutic peptide may differ from each other while they encode the same therapeutic peptides having the same amino acid sequence.

The pharmaceutical composition of the present invention may further include a pharmaceutically acceptable carrier or pharmaceutically acceptable salt. Meanwhile, the pharmaceutical composition may further include chemotherapeutic agents, such as 5-fluorouracil (5-FU), UFT (tegafur-uracil), capecitabine, irinotecan, oxaliplatin, bevacizumab (trade name: Avastin), and cetuximab (trade name: Erbitux).

The composition of the present invention is preferably administered by a route that is most effective for treatment. The composition may be administered orally or by parenteral routes, such as intraoral, tracheobronchial, intrarectal, subcutaneous, intramuscular and intravenous routes. Dosage forms include sprays, capsules, tablets, granules, syrups, emulsions, suppositories, injections, ointments, tapes, and the like.

For oral administration, gastroresistant oral dosage forms may be formulated, which may also include compounds providing controlled release of the host cells and thus provide controlled release of the desired therapeutic peptide encoded therein. For example, the oral dosage form (including tablets, pellets, granulates, and powders) may be coated with a thin layer of excipient (usually polymers, cellulosic derivatives and/or lipophilic materials) that resists dissolution or disruption in the stomach, but not in the intestine, thereby allowing transit through the stomach in favor of disintegration, dissolution and absorption in the intestine.

The oral dosage form may be designed to allow slow release of the host cells and of the recombinant protein thereof, for instance as controlled release, sustained release, prolonged release, sustained action tablets or capsules. These dosage forms usually contain conventional and well known excipients, such as lipophilic, polymeric, cellulosic, insoluble, swellable excipients. Controlled release formulations may also be used for any other delivery sites including intestinal, colon, bioadhesion or sublingual delivery (i.e., dental mucosal delivery) and bronchial delivery.

Preparations suitable for oral administration include emulsions, syrups, capsules, tablets, powders, granules and the like. Liquid preparations such as emulsions or syrups may be prepared using, as additives, water, sugars such as sucrose, sorbitol and fructose, glycols such as polyethylene glycol and propylene glycol, oils such as sesame oil, olive oil and soybean oil, antiseptics such as p-hydroxybenzoates, flavors such as strawberry flavor and peppermint, and the like. Capsules, tablets, powders, granules, and the like may be prepared using, as additives, excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, plasticizers such as glycerin, and the like.

Preparations suitable for parenteral administration include injections, suppositories, sprays and the like. Injections are prepared using carriers including a salt solution, a glucose solution, or a mixture thereof. Alternatively, powdery injections may also be prepared by freeze-drying the strain according to a conventional method and adding sodium chloride thereto. Suppositories are prepared using carriers such as cacao butter, hydrogenated fat or carboxylic acid. In addition, sprays are prepared using the compound itself and carriers which do not stimulate the oral and airway mucous membranes of a recipient and which disperse the compound into fine particles which are easily absorbed.

The dose of the therapeutic peptide-producing strain which is the active ingredient of the pharmaceutical composition according to the present invention may vary depending on the patient's age, sex, body weight and disease. However, the strain may be administered once or several times at a dose of 0.001 to 100 mg/kg, preferably 0.01 to 10 mg/kg.

In addition, the dose of the strain according to the present invention may be increased or decreased depending on the route of administration, the severity of the disease, the patient's sex, body weight, age and the like. Accordingly, the dose is not intended to limit the scope of the present invention in any way.

The present invention will be described in more detail below with reference to examples. However, these examples are for illustrative purposes only, and the scope of the present invention is not limited by these examples.

EXAMPLES

Example 1. Construction of System for Overexpression and Secretion of Lactic Acid Bacteria-Derived Protein Example 1-1. Selection of Promoters for Induction of Overexpression Six strong promoters (ermE, erythromycin resistance gene promoter; PK, pyruvate kinase; GK, glucokinase; GPFK, 6-phosphofructokinase; G6Pi, glucose 6-phosphoate isomerase; and L-LDH, L-lactate dehydrogenase) for expression of a target protein (P8 protein A) in lactic acid bacteria were selected from the glycolysis metabolic pathway of *Pediococcus pentosaceus*. Experiments demonstrated that the glucose consumption rate of the host was very high, and HPLC analysis indicated that nearly 100% of the consumed glucose was converted to the secondary metabolite L-lactate. For this reason, of the promoters, five were selected from the glycolysis metabolic pathway, and one was selected from the secondary metabolite lactate production pathway.

Example 1-2. Construction of System for Overexpression and Secretion of Target Protein The plasmid pCBT24-2 (SEQ ID NO: 9) (KCCM12182P) was used for cloning of the P8 protein. The promoters selected in Example 1-1 were ligated with a usp45 signal peptide, thereby synthesizing DNA fragments. BamHI/PstI restriction enzyme sites were inserted into each promoter ligated with the signal peptide. After completion of the synthesis, a portion of each promoter ligated with the signal peptide was digested with BamHI/PstI restriction enzymes, and the DNA fragments were isolated/purified by DNA gel extraction, and each of the DNA fragments was inserted into a pCBT24-2-P8/BamHI/PstI vector digested with the same restriction enzymes. Each of the constructed pCBT24-2-PK-P8, pCBT24-2-GK-P8, pCBT24-2-6PFK-P8, pCBT24-2-FK-PB, pCBT24-2-G6Pi-P8, pCBT24-2-L-LDH-P8 and pCBT24-2-D-LDH-P8 was transformed into a *Pediococcus pentosaceus* SL4 strain.

The promoters that showed high activity in the previous step were combined with each other, thereby constructing pCBT24-2-GK-P8-L-LDH-oriP8, pCBT24-2-PK-P8-PK-oriP8, and pCBT24-2-GK-P8-GK-oriP8. Each of the constructed DNAs was transformed into the *Pediococcus pentosaceus* SL4 strain.

Among the strains of the present invention, the strain transformed with pCBT24-2-PK-P8-PK-oriP8 was named PP P8 and deposited in the Korean Culture Center of Microorganisms (KCCM), located at Yurim B/D Hongjenae-2ga-gil, Seodaemun-gu, Seoul, Korea, on Nov. 30, 2017 under the provisions of the Budapest Treaty with accession number KCCM12181P.

The transformant was mixed with LB liquid medium, and then cultured at 37° C. for 1 hour. The transformant cultured for 1 hour was plated onto LB agar medium containing erythromycin (final concentration: 10 μg/ml), and a strain showing resistance to the antibiotic was selected as a strain (PP DDS) to be used as a drug delivery system in the present invention.

Example 1-3. Culture of *Pediococcus pentosaceus* SL4 Transformant

The transformant grown on MRS solid medium (agar plate) was inoculated into 10 ml of MRS liquid medium (containing 10 mg/ml of erythromycin) and statically cultured at 37° C. for 15 hours (overnight incubation). 1 ml of the culture was inoculated into 10 ml of M9 minimal medium (containing 10 mg/L of erythromycin) and then statically cultured at 37° C. for 48 hours. 5 ml of the culture was centrifuged, and the supernatant was collected. 5 ml of the supernatant was concentrated by TCA precipitation to isolate total protein. Using the total protein, the expression and secretion levels of the P8 protein were comparatively analyzed by Western blotting. The microbial cells were diluted with buffer and lysed using a sonicator, and then the cell extract was analyzed by Western blotting, thereby determining the amount of P8 protein that was not secreted after expression.

Example 1-4. Isolation and Detection of P8 Protein

The lactic acid bacteria transformant was cultured, and then 100% TCA (Trichloro Acetic Acid) was added to 5 ml of the culture supernatant to a final concentration of 20%. After mixing, the solution was incubated on ice for 30 minutes, and centrifuged at 15,000 rpm and 4° C. for 30 minutes to induce the precipitation of all proteins. After centrifugation, the supernatant was removed, and 200 μl of acetone was added, to the precipitate which was then centrifuged at 15,000 rpm and 4° C., and the precipitated protein was washed. After the remaining acetone was completely removed by drying at room temperature, the secretion level of the target protein present in the culture supernatant was measured. The secretion level was measured by Western blotting, and the results of the measurement are shown in FIGS. 4 to 7.

Figure 7:
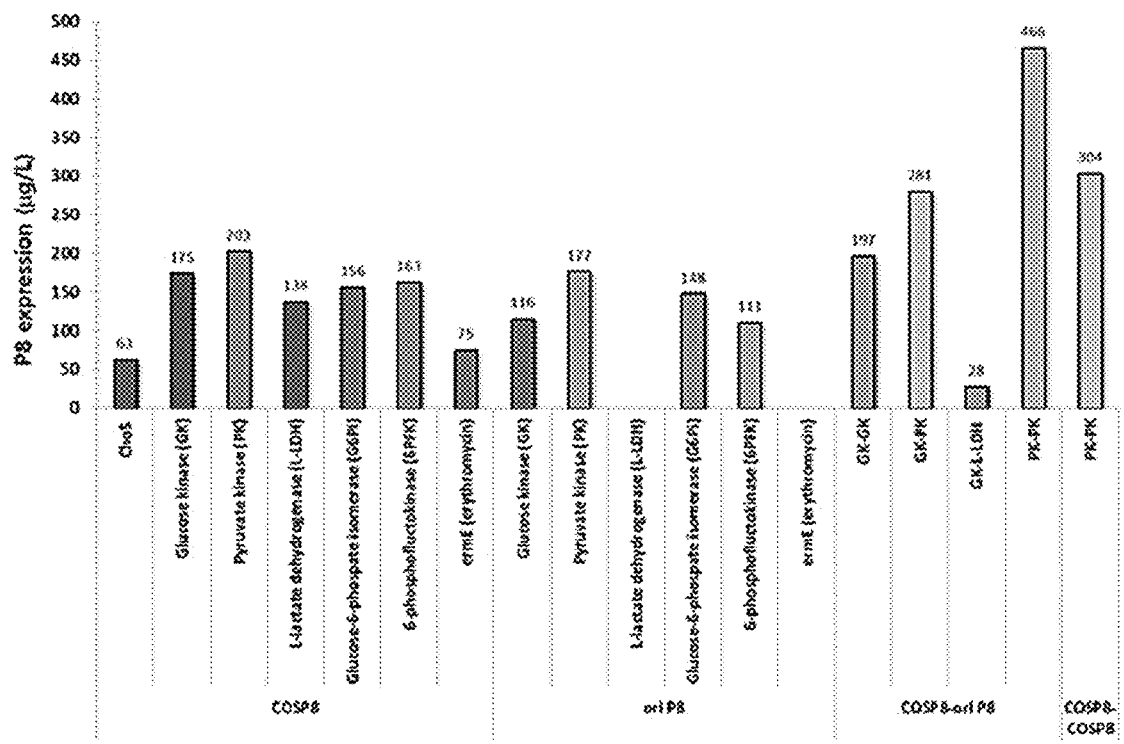
FIG. 7 is a graph showing the results of ELISA performed to quantitatively analyze the changes in expression/secretion levels of P8 protein by various promoter combinations according to the present invention.

Referring to FIGS. 4 to 7, it was shown that the use of the promoters of the present invention significantly increased the expression and secretion levels of the P8 protein. In particular, as can be seen in FIG. 7, the use of the two promoters (PK-PK, GK-PK, and GK-GK) showed the highest expression and secretion levels of the P8 protein.

Example 2. Evaluation of Anticancer Effect of P8 Protein by Use of In Vivo Lactic Acid Bacteria Expression/Secretion System

Example 2-1. Tumor Cell Transplantation and Tumor Transplantation

The colorectal cancer cell line DLD-1 obtained from the Korean Cell Line Bank (Seoul, Korea) was subcultured at 37° C. in a 5% $CO_2$ incubator with RPMI 1640 medium (Sigma, MO, USA) containing 10% fetal bovine serum (FBS; Invitrogen, NY, USA), penicillin (0.02 UI/ml; Sigma, MO, USA), streptomycin (0.02 μg/ml; Sigma, MO, USA), glutamine (2 mM: Sigma, MO, USA) and non-essential amino acid (1%; Sigma, MO, USA). The cultured DLD-1 cells were suspended, and the tumor cell suspension were transplanted subcutaneously into the back of male nude mice (BALB/cAnN.Cg-Foxn1nu/CrlNarl; 5 weeks old) in an amount of 0.2 ml ($2×10^6$ cells/mouse), thereby forming solid tumors. To dissect tumor tissue formed from the subcultured group, the animals were sacrificed and the tumor lumps were dissected. The blood vessels and fat layer distributed on the surface were removed, and then only fresh tumor tissue was selected and transplanted subcutaneously into untreated animals by a troca needle.

Example 2-2. Division into Experimental Groups and Substance Administration

When the volumes of individual tumors reached 100-150 $mm^3$ after transplantation of the tumor lumps, the body weights and the tumor sizes were measured, and the animals were randomly grouped. The experimental animals were divided into a total of seven groups as shown in Table 3 below, and each group consisted of, 10 animals: a negative control group (tumor-transplanted control group: G1); a positive control group (a group administered with an anti-cancer agent, 40 mg/Kg 5-Fu; 5-fluorouracil, Sigma, MO, USA: G2), and experimental groups {a group administered with $1×10^{10}$ CFU/head (a group administered with drug delivery system (DDS) *P. pentosaceus* (empty vector)): G3; a group administered with $1×10^9$ CFU/head PP-DDS (PK-P8-ChoS-oriP8): 2-promoter system: G4; a group administered with $1×10^{10}$ CFU/head PP-DDS (PK-P8-ChoS-oriP8): 2-promoter system: G5; a group administered with $1×10^9$ CFU/head PP-DDS (PK-P8-PK-oriP8): 2-promoter system: G6; and a group administered with $1×10^{10}$ CFU/head PP-DDS (PK-P8-PK-oriP8: 2-promoter system: G7). Each of the groups was administered orally with the indicated substance once a day for 7 weeks. Here, the transformant was cultured in MRS medium and suspended to a concentration of $10^{10}$/200 μl, and the suspension was administered orally once a day for a total of 6 weeks.

TABLE 3

| Group | Treatment | | Number of animals |
|---|---|---|---|
| G1 (NC1) | Treated with PBS | 100 μl/head | 10 |
| G2 (PC1) | 5-fluorouracil (5-Fu) | 400 μg/head | 10 |
| G3 (T1) | Empty vector | $1 × 10^{10}$ CFU/head | 10 |
| G4 (T2) | PP-DDS (PK-P8-ChoS-oriP8) | $1 × 10^9$ CFU/head | 10 |
| G5 (T3) | PP-DDS (PK-P8-ChoS-oriP8) | $1 × 10^{10}$ CFU/head | 10 |
| G6 (T4) | PP-DDS (PK-P8-PK-oriP8) | $1 × 10^9$ CFU/head | 10 |
| G7 (T5) | PP-DDS (PK-P8-PK-oriP8) | $1 × 10^{10}$ CFU/head | 10 |
| Total number of animals | | | 70 |

Example 2-3. Measurement of Change in Volume of Solid Cancer

The growth of tumors in the seven groups of nude mice BALB/cAnN.Cg-Foxn1nu/CrlNarl; 5 weeks old) (10 animals per group) transplanted with the colorectal cancer cell line DLD-1 was confirmed, and the tumor lumps transplanted subcutaneously into the right sides manifested as subcutaneous nodules 5 days after transplantation.

After tumor tissue transplantation, the animals were grouped as shown in Table 3 above and were treated according to the dosage schedule. During the period from the $0^{th}$ day before administration to the 49th day after administration, the sizes of the tumor tissues were measured once a week with Vernier calipers. On the 49th day of the experiment, the xenograft models (solid cancer models) were sacrificed, and tissue samples were obtained, after which tumor metastasis was observed. The tumor volume was calculated using the following equation: width$^2$× length/2 (mm$^3$). The measured tumor sizes are shown in FIG. 8.

Figure 8:
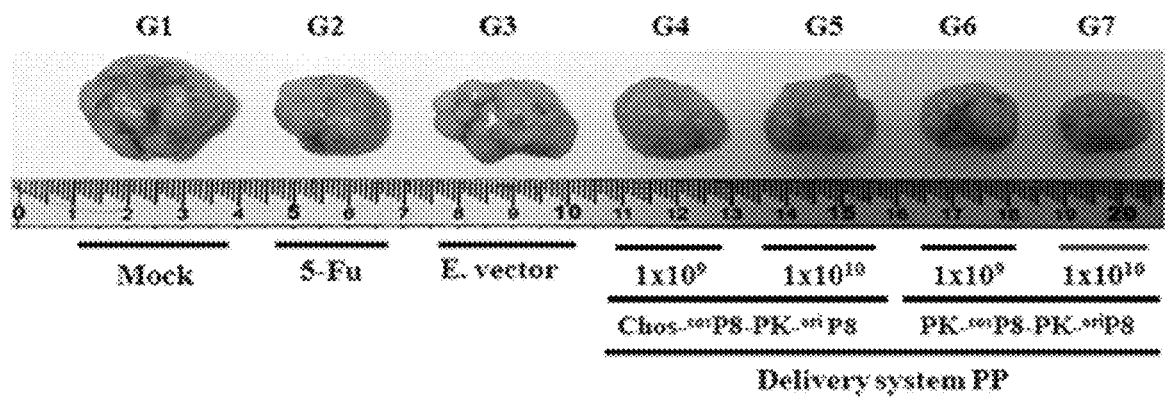
FIG. 8 is a photograph comparing the anticancer activities after oral administration of recombinant strains according to the present invention.

Referring to FIG. 8, the anticancer effects of the P8 protein were compared between the *Pediococcus pentosaceus* drug delivery system (PP-DDS) (PK-P8-ChoS-oriP8) 2-promoter system and the PP-DDS (PK-P8-PK-oriP8) 2-promoter system. At the same dose (1×10$^{10}$ CFU/head), the anticancer activity of administration of the *Pediococcus pentosaceus* drug delivery system (PP-DDS) (PK-P8-ChoS-oriP8) (49.4% anticancer activity) was about 5% higher than that of the *Pediococcus pentosaceus* drug delivery system (PK-P8-PK-oriP8) (44.6% anticancer activity).

The tumor size in the groups (G4 and G5) administered with the drug delivery system *Pediococcus pentosaceus* strain (KCCM12181P) of the present invention, which expresses and secretes the P8 protein, significantly decreased compared to those in the negative control group (G1) and the positive control group (G3), and decreased to a size similar to that in the group (G2) administered with 5-fluorouracil (5-Fu). Meanwhile, particularly, in the groups (G6 and G7) administered with high concentrations of the strain having the two promoters, the tumor size greatly decreased compared to that in the group (G2) administered with 5-fluorouracil (5-Fu), indicating that the strain exhibited very excellent anticancer activity.

Example 2-4. Examination of Survival of PP DDS in Mouse Intestines and Stability of Plasmid DNA In order to examine whether the drug delivery system *Pediococcus pentosaceus* strain (KCCM12181P) that expressed/excreted the P8 protein could reach mouse intestines alive after administration to mice, the *Pediococcus pentosaceus* strain was administered to mice. After 6 weeks, mouse intestinal contents were collected and cultured on MRS (10 μg/ml of erythromycin) plates, and the amount of the *Pediococcus pentosaceus* strain present in the mouse intestinal contents was analyzed. The expression and secretion levels of the P8 protein from the survived *Pediococcus pentosaceus* strain were measured.

Figure 9:
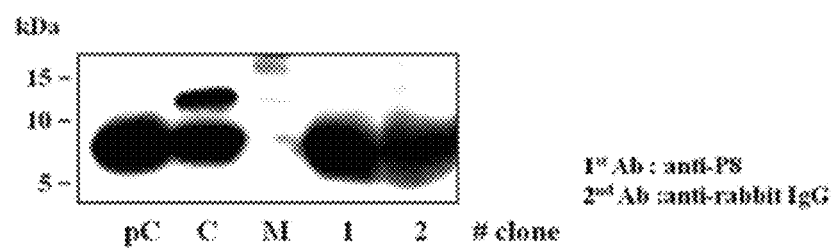
FIG. 9 is a photograph showing the results of detecting a P8 protein from a P8 protein-expressing and -secreting *Pediococcus pentosaceus* strain of the present invention, isolated from the small intestines of nude mice administered with a pharmaceutical composition of the present invention.

After the completion of the 6-week experiment, the contents in the mouse small intestines were collected and washed twice with PBD buffer, followed by centrifugation. The remaining supernatant was concentrated by 20% TCA and analyzed by Western blotting to detect the P8 protein. The results of the analysis are shown in FIG. 9. In FIG. 9, pC shows the result of Western blotting performed on the culture supernatant of the *Pediococcus pentosaceus* strain with pCBT24-2-ChoS-COSP8. C shows the result of Western blotting performed on the purified P8 protein; 1 shows the result of Western blotting performed on the cultured *Pediococcus pentosaceus* strain grown in the content collected from the intestine; and 2 shows the result of Western blotting performed on the cultured *Pediococcus pentosaceus* strain grown in the content collected from the intestine.

Referring to FIG. 9, although the amount of P8 protein detected could not be quantitatively analyzed and the actual amount thereof could not be determined, the P8 protein was detected. This indirectly confirms that the *Pediococcus pentosaceus* strain that expressed/secreted the P8 protein continuously expressed and secreted the P8 protein after it was colonized in the mouse intestines.

The use of lactic acid bacteria as therapeutic agents against colorectal diseases, including colorectal cancer, colitis, irritable bowel syndrome, Crohn's disease and the like, is known technology. However, there has been little development regarding a system for overexpression and secretion of a target protein from lactic acid bacteria and the use of the system as a drug delivery system. In the present invention, the protein derived from lactic acid bacteria was introduced into the lactic acid bacteria expression/secretion system, thereby developing the lactic acid bacteria drug delivery system that overexpresses and secretes the protein, and the effect of the drug delivery system was demonstrated by applying it to animal models. Accordingly, it is expected that the present invention will be widely used as a natural therapeutic agent for treatment of colorectal disease in the medical field.

Although the preferred embodiments of the present invention have been described in detail, the present invention is not limited to the above-described embodiments. Those skilled in the art to which the present invention pertains will appreciate that various modifications and alterations may be easily made based on the above-described embodiments. Therefore, the true scope of protection of the present invention should be defined based on the appended claims and their equivalents.

The invention claimed is:

1. A *Pediococcus pentosaceus* strain for treating colorectal cancer, comprising a DNA construct that comprises:
   an exogenous promoter;
   a polynucleotide encoding a P8 protein operably linked to the exogenous promoter and having the nucleotide sequence represented by SEQ ID NO: 1; and
   a gene encoding a secretion signal peptide,
   wherein the *Pediococcus pentosaceus* strain is capable of expressing and secreting the P8 protein in a gastrointestinal tract, and
   the exogenous promoter is at least one promoter selected from the group consisting of SEQ ID NO: 3 to SEQ ID NO: 8.

2. The *Pediococcus pentosaceus* strain of claim 1, wherein the secretion signal peptide is a USP45 secretion signal peptide, Usp45 N4, or a *Lactobacillus brevis* S-layer protein signal peptide.

3. The *Pediococcus pentosaceus* strain of claim 2, wherein the secretion signal peptide is the USP45 secretion signal peptide.

4. The *Pediococcus pentosaceus* strain of claim 1, wherein the DNA construct further comprises
   a second secretion signal peptide and a heterologous nucleic acid sequence encoding a second therapeutic peptide,
   wherein the second secretion signal peptide and the heterologous nucleic acid sequence are disposed downstream of the exogenous promoter.

5. A pharmaceutical composition for treatment of colorectal cancer, comprising the *Pediococcus pentosaceus* strain of claim 1, which is capable of producing and secreting a P8 protein having the amino acid sequence represented by SEQ ID NO: 2.

6. The *Pediococcus pentosaceus* strain of claim 1, wherein the *Pediococcus pentosaceus* strain is deposited in the Korean Culture Center of Microorganisms (KCCM) under the accession number KCCM12181P.

7. The pharmaceutical composition of claim 5, wherein the *Pediococcus pentosaceus* strain is deposited in the Korean Culture Center of Microorganisms (KCCM) under the accession number KCCM12181P.

8. The *Pediococcus pentosaceus* strain of claim 4, wherein the exogenous promoter includes a first promoter and a second promoter, and the second promoter is identical to the first promoter.

9. The *Pediococcus pentosaceus* strain of claim 4, wherein the exogenous promoter includes a first promoter and a second promoter, and the second promoter is different from the first promoter.

* * * * *

SEQUENCE LISTING

```
<160> NUMBER OF SEQ ID NOS: 9

<210> SEQ ID NO 1
<211> LENGTH: 219
<212> TYPE: DNA
<213> ORGANISM: Artificial Sequence
<220> FEATURE:
<223> OTHER INFORMATION: Protein P8

<400> SEQUENCE: 1
gcaacagtag atcctgaaaa gacattgttt ctcgatgaac caatgaacaa ggtatttgac      60
tggagcaaca gcgaagcacc tgtacgtgat gcgctgtggg attattacat ggaaaagaac     120
agccgtgata ccatcaagac tgaagaagaa atgaaaccag tcctagacat gtccgacgat     180
gaggtcaaag ccctagcaga aaaggttctc aagaagtaa                            219
```

```
<210> SEQ ID NO 2
<211> LENGTH: 72
<212> TYPE: PRT
<213> ORGANISM: Artificial Sequence
<220> FEATURE:
<223> OTHER INFORMATION: Protein P8

<400> SEQUENCE: 2

Ala Thr Val Asp Pro Glu Lys Thr Leu Phe Leu Asp Glu Pro Met Asn
1               5                   10                  15

Lys Val Phe Asp Trp Ser Asn Ser Glu Ala Pro Val Arg Asp Ala Leu
            20                  25                  30

Trp Asp Tyr Tyr Met Glu Lys Asn Ser Arg Asp Thr Ile Lys Thr Glu
        35                  40                  45

Glu Glu Met Lys Pro Val Leu Asp Met Ser Asp Asp Glu Val Lys Ala
    50                  55                  60

Leu Ala Glu Lys Val Leu Lys Lys
65                  70

<210> SEQ ID NO 3
<211> LENGTH: 184
<212> TYPE: DNA
<213> ORGANISM: Artificial Sequence
<220> FEATURE:
<223> OTHER INFORMATION: Promotor ermE

<400> SEQUENCE: 3 ggatccttttt tagtattttt aattaattgt aatcagcaca gttcattatc aaccaaacaa      60
aaaataagtg ttataatga atcgttaata agcaaaattc atataaccaa attaagaagg       120
gttataatga aaaaaaagat tatctcagct attttaatgt ctacagtgat actttctgct      180
gcag                                                                   184

<210> SEQ ID NO 4
<211> LENGTH: 324
<212> TYPE: DNA
<213> ORGANISM: Artificial Sequence
<220> FEATURE:
<223> OTHER INFORMATION: Promotor PK

<400> SEQUENCE: 4
ggatccctaa agatcgcgtt ttagcaagta agatgggtgc ttacgctgtt gagctactcc      60
ttgaaggtaa gggtggttta gcagttggaa tcttagaaaa taaggttcaa gctcataaca     120
tgcttgactt gtttgatgca aaacatcaag cagatgattc actttaccaa ttaagtgaag    180
atttatcatt ctagagttct attaatattt ggataaaatg acttaagaag tcttttataa    240
tttaaaatca agggagagat tctgtaatga aaaaaaagat tatctcagct attttaatgt    300
ctacagtgat actttctgct gcag                                            324

<210> SEQ ID NO 5
<211> LENGTH: 324
<212> TYPE: DNA
<213> ORGANISM: Artificial Sequence
<220> FEATURE:
<223> OTHER INFORMATION: Promotor GK

<400> SEQUENCE: 5
ggatccataa tctggtaaat tagttgagat ggtattatga aaacacttta tgatgtgcaa      60
caacttttaa agcaattcgg aatatttgtt tacgttggaa aacgtaaatg ggatattgaa     120
ttgatgagta ttgaattgaa aaatttgtac aaagcaggag tcgtcgataa accgacttat    180
```

```
gttaaagctc agttggtttt acgacatgag catcatattg aagaggttag agataaccaa    240
caaaaataat ggagggtttc gaagtaatga aaaaaaagat tatctcagct attttaatgt    300
ctacagtgat actttctgct gcag                                           324
```

```
<210> SEQ ID NO 6
<211> LENGTH: 324
<212> TYPE: DNA
<213> ORGANISM: Artificial Sequence
<220> FEATURE:
<223> OTHER INFORMATION: Promotor GPFK

<400> SEQUENCE: 6
ggatccccag ttattttagt ttatgaggat actaatgaac ataatgagtt gtctgaaaaa    60
ttttatttaa atgacagttc tgaagtaaaa gaacaattag cagaattgct aggaagtcaa    120
catatttcgt taattaaaaa ataaattttg ataaagcac ttacattcga ttaattaaga    180
aaatggtaca gacaactgtt ttcaaaagtg ataaaatcaa caatgaagtt ttgaaaaaac    240
tcaatatttc tgtttgaggt gaaagatga aaaaaaagat tatctcagct attttaatgt    300
ctacagtgat actttctgct gcag                                           324
```

```
<210> SEQ ID NO 7
<211> LENGTH: 324
<212> TYPE: DNA
<213> ORGANISM: Artificial Sequence
<220> FEATURE:
<223> OTHER INFORMATION: Promotor G6Pi

<400> SEQUENCE: 7
ggatccatgc cggctaaagt ggtggataaa ttgaatcatc cccaagaact ggaataagat    60
aaaattgtag tgcttttcagg ctttaccagc catcttttga aaaaattaat ttcttttcaaa  120 agtgcgtgtg acaggtgatc aactagatta aatggggagg gtatcccagt aaatattagg    180
ttaaatcgga taggcttaac caaattaagt aattttattg tataatggta cagataaaga    240
attttaaaca aaggggtag ttattaatga aaaaaaagat tatctcagct attttaatgt    300
ctacagtgat actttctgct gcag                                           324
```

```
<210> SEQ ID NO 8
<211> LENGTH: 324
<212> TYPE: DNA
<213> ORGANISM: Artificial Sequence
<220> FEATURE:
<223> OTHER INFORMATION: L-LDH

<400> SEQUENCE: 8
ggatcctcat ttcatgtta tttttccacc ctcaacacgc aaaaacggct gaaagagcaa    60 aaaccccctca gctgtccacg tttattttca tgtaatatta ccatattatt gaccccaagc    120
gggtctttta acctctaact tatcaatcac tttactaact atacccgaac ttcataaaat    180
ttttactcaa ctttctttta tgaaaatgct atacttagta ttgtttgata aattcaaata    240
ttatatgaaa aaaggggatt gatcttatga aaaaaaagat tatctcagct attttaatgt    300
ctacagtgat actttctgct gcag                                           324
```

```
<210> SEQ ID NO 9
<211> LENGTH: 4757
<212> TYPE: DNA
<213> ORGANISM: Artificial Sequence
<220> FEATURE:
<223> OTHER INFORMATION: pCBT24-2
```

<400> SEQUENCE: 9

```
aagttaatgt aagccttaag gtttcaacta aagcaattac ggtcaaccat aaccatagta      60
ttggattgtc attttattgg ctataaaata gtaaatcagt gaatttcatt ggatccgcta     120
aagatcgcgt tttagcaagt aagatgggtg cttacgctgt tgagctactc cttgaaggta     180
agggtggttt agcagttgga atcttagaaa ataaggttca agctcataac atgcttgact     240
tgtttgatgc aaaacatcaa gcagatgatt cactttacca attaagtgaa gatttatcat     300
tctagagttc tattaatatt tggataaaat gacttaagaa gtcttttata atttaaaatc     360
aagggagaga ttctgtaatg aaaaaaaaga ttatctcagc tattttaatg tctacagtga     420
tactttctgc tgcagccccg ttgtcaggtg tttacgctga agtaattatt atggctaccg     480
ttgatccaga aaagactcta ttccttgatg aaccaatgaa taaagttttt gattggtcta     540
acagtgaggc tccggtgcga gatgccttat gggattacta tatggaaaag aatagccgtg     600
acacgatcaa aacagaagaa gaaatgaaac ctgtattaga tatgtcagat gacgaagtta     660
aagcattagc ggagaaagtc ttgaaaaagt aacctgacaa gaaccagtct gctattgata     720
gactattttt gtccgtgaaa tcctcgcgta tttccgtgag gagcatagta tatttagcga     780
tcttcaaatt ttaagtatat tgattcatat gtttatcctc ctaagtttga ggacaaatcg     840
gattccacgg cctcaatgac tgagctccgc ctattttat aggttaatgt catgataata     900
atggtttctt agcgattcac aaaaaatagg cacacgaaaa acaagttaag ggatgcagtt     960
tatgcatccc ttaacttact tattaaataa tttatagcta ttgaaaagag ataagaattg    1020
ttcaaagcta atattgttta aatcgtcaat tcctgcatgt tttaaggaat tgttaaattg    1080
attttttgta aatattttct tgtattcttt gttaacccat ttcataacga aataattata    1140
cttttgttta tctttgtgtg atattcttga ttttttttcta cttaatctga taagtgagct    1200
attcactta ggtttaggat gaaaatattc tcttggaacc atacttaata tagaaatatc    1260
aacttctgcc attaaaagta atgccaatga gcgttttgta tttaataatc ttttagcaaa    1320
cccgtattcc acgattaaat aaatctcatt agctatacta tcaaaaacaa ttttgcgtat    1380
tatatccgta cttatgttat aaggtatatt accatatatt ttataggatt ggttttttagg    1440
aaatttaaac tgcaatatat ccttgtttaa aacttggaaa ttatcgtgat caacaagttt    1500
attttctgta gttttgcata atttatggtc tatttcaatg gcagttacga aattacacct    1560
ctttactaat tcaagggtaa aatggccttt tcctgagccg atttcaaaga tattatcatg    1620
ttcatttaat cttatatttg tcattatttt atctatatta tgttttgaag taataaagtt    1680
ttgactgtgt tttatatttt tctcgttcat tataaccctc tttaatttgg ttatatgaat    1740
tttgcttatt aacgattcat tataaccact tattttttgt ttggttgata atgaactgtg    1800
ctgattacaa ttaattaaaa atactaaaaa tgcccatatt ttttcctcct tataaaatta    1860
gtataattat agcacgaaaa ggatctaggt gaagatcctt tttgataatc tcatgaccaa    1920
aatcccttaa cgtgagtttt cgttccactg agcgtcagac cccgtagaaa agatcaaagg    1980
atcttcttga tccttttttt ttctgcgcgt aatctgctgc ttgcaaacaa aaaaaccacc    2040
gctaccagcg gtggtttgtt tgccggatca agagctacca actctttttc cgaaggtaac    2100
tggcttcagc agagcgcaga taccaaatac tgttcttcta gtgtagccgt agttaggcca    2160
ccacttcaag aactctgtag caccgcctac atacctcgct ctgctaatcc tgttaccagt    2220
ggctgctgcc agtggcgata gtcgtgtct taccggttg gactcaagac gatagttacc    2280
ggataaggcg cagcggtcgg gctgaacggg gggttcgtgc acacagccca gcttggagcg    2340
```

```
aacgacctac accgaactga gatacctaca gcgtgagcta tgagaaagcg ccacgcttcc    2400
cgaagggaga aaggcggaca ggtatccggt aagcggcagg gtcggaacag gagagcgcac    2460
gagggagctt ccaggggaa acgcctggta tctttatagt cctgtcgggt ttcgccacct     2520
ctgacttgag cgtcgatttt tgtgatgctc gtcaggggg cggagcctat ggaaaaacgc    2580
cagcaacgcg gccttttac ggttcctggc cttttgctgg ccttttgctc acatgttctt     2640
tcctgcgtta tccctgatt ctgtggataa ccgtattacc gcctttgagt gagctgatac    2700
cgctcgccgc agccgaacga ccgagcgcag cgagtcagtg agcgaggaaa tcgatactga    2760
attggcgaaa gccaaagttt ctataaaacc ttgctttcct gcttaacggc gagtgaaaaa     2820
gcggttaagc tggctcagct tggacggggt tcgggcgtt agcgtccgta ttaaatgtgg    2880
cttaccataa ccaacgaaca gagtgaggtg caaggagctg tgcgactgga gtttaatgtg    2940
agccggtttt tggctcactc ctttgtgttt tttgtttcta gattttaatc tcgtacagcg    3000
gtgcctcttt tatacctctt ttataaacct cttttaaacc tcttttagac ccctcttgag    3060
ccttactctc ccaaggctca cagaaggtta tcaagtacct tttgtctgtt tatcaagtac    3120
cttttgtctg tttatcaagt accttttgtc tgtttatcaa gtaccttttg tctgtttatc    3180
aagtaccttt ataagttctg tacttgataa aaaggtactt ttattttaat atgtgtttga    3240
ggtgataatc atggctaatg agtagttaa gtatgatcct gagttgaata ctattccctt    3300
gagaaaattt accccaattg agatgaattt attttttca attatttccc gcatgcggga    3360
tcaagggaat aaaactgttc gtttctcttt tgaccagtta aaagagctta gtaactataa    3420
accaaccgca aataaacgtt ttattgatga tattgaaaat ataccaaa agatcctcag     3480 ccttaggttt ggccgtagaa gtaagagtgg cttaaatcgt gaattttttg ttatgtttac    3540
tgaatttgaa attaaaggtg aagctgaaga accttatgtt gatattcaga tttatcccaa    3600
agcattgcac ttgctaaacg atttagaaag ttgggttcgt tatgccctaa cagaatttag    3660
aaatttaaaa agcagttacg ctaaaacaat gtttcgtcta attaagcaat ttcgaactac    3720
tggctattct tatttctcta agaagatttt ttttgaattg cttgatatac ctaaaagtta    3780
ttggaatagt ccttcaaagg ttgacaaaaa ggttattaag ccaattagag aagaattaac    3840
cccgcttttt agagggctaa cgattagaaa aaaatatggt aaaggcagag gaaaaccagt    3900
tatcggttat tcttttactt ggaaacctga aagcaaggac gcaaatgatt tttctcaagg    3960
caaatttcaa gatgagcgtc aaaaactctt taacattcag cacaatgatg aattatcaga    4020 taaagaaag tggcgtgcaa ttgacaaagt taaatgcttg cctttaggaa caactgaaaa    4080
acaggtactg gctgaaaaac aagctgaaca tgatcaaaaa atcagagatc aagcaagaca    4140
agaatttctc gctgatctcc gaaagggggtt ttaaaatcat gtctaaaact attagagaac    4200
ttgctgatga attgaatgtc tccaaacaga ctattcaata tcactaccaa agactaccag    4260
caaagaacca acaaaagaat agtcagggca caaaccttat tagtcctaca gcagaaagaa    4320
ttataagaag caaggtagca aagccttgc tagcaaaaaa acagcaaaga ggtagcaaag    4380
aattgccaaa gactagcaaa gaaaataatg atctggttgc tactctgaga agagaagtag    4440
aagatttaaa ggctcaacgt gacaaacagc ttgctaccaa agaccgacaa atagaccatc    4500
taacaaaatt ggtggatcag cagcaacaat tacaattagc aacagtagca gataaccgtc    4560
gattaaaaga tcatgtacaa aagctaagtg ggcaactaac tcaaaaaact aacgacaact    4620
tgtcgaccgg aaatgatctt tttaacatcc aagataaaga aagcaaaata gctaaacaga    4680
```

```
agattgttaa atctggtagt aataaagatg gcatacacac aaatagagct attaaacgtt    4740
ggtggaaatt ctggtaa                                                   4757
```